United States Patent [19]

Martens et al.

[11] Patent Number: 4,583,686
[45] Date of Patent: Apr. 22, 1986

[54] PACKAGE FOR DISPENSING VOLATILES

[75] Inventors: Edward J. Martens; Gerald H. Schuebel, both of Racine County, Wis.

[73] Assignee: S. C. Johnson & Son, Inc., Racine, Wis.

[21] Appl. No.: 644,596

[22] Filed: Aug. 27, 1984

[51] Int. Cl.⁴ ............................................. A61L 9/04
[52] U.S. Cl. ........................................ 239/35; 239/34; 239/51.5
[58] Field of Search ............ 239/34, 35, 44, 47, 239/51.5, 53–59; 206/0.5

[56] References Cited

U.S. PATENT DOCUMENTS

| | | | |
|---|---|---|---|
| 2,239,628 | 4/1941 | Seki | 239/44 |
| 2,530,340 | 11/1950 | Sager | 239/35 |
| 2,545,160 | 3/1951 | Miller | 239/55 |
| 3,797,742 | 3/1974 | Clark et al. | 239/57 |
| 3,858,807 | 1/1975 | Rabussier et al. | 239/57 |
| 3,908,,905 | 9/1975 | Von Philipp et al. | 239/55 |
| 4,157,787 | 6/1979 | Schwartz | 239/56 |

*Primary Examiner*—Jeffrey V. Nase

[57] ABSTRACT

An air-treating article of the type having an enclosed volatile composition which will permeate through a film to be dispensed to the atmosphere. A grill-like cover member protects the film from human contact and a peelable impermeable strip under the cover member is adhered to the film until it is peeled away by means of a leader. The leader is attached at its proximal end to one end of the strip, overlies the strip under the cover member, and terminates in a gripping end outside the cover member. The strip may be peeled away to expose the film while the cover member remains in place protecting the film. In preferred embodiments the composition is a free liquid, and a use-up indicator is provided.

10 Claims, 5 Drawing Figures

PACKAGE FOR DISPENSING VOLATILES

FIELD OF THE INVENTION

The invention is related generally to products for dispensing air-treating vapors into the atmosphere and, more particularly, to devices for continuously dispensing volatile compositions to the atmosphere through permeable films.

BACKGROUND OF THE INVENTION

Volatile substances, such as perfumes and deodorizers, are commonly employed as room air fresheners. A variety of packages have been used to contain volatile liquids and continuously dispense them as vapors into the atmosphere. Among these are: old-style products such as those utilizing a glass bottle and a wick; the more recent packet-type products which enclose a breakable impermeable capsule or bag of volatile material within a permeable envelope; and the formed plastic-box type products having a permeable film surface and a peelable cover laminated thereto the removal of which initiates dispensing of vapors.

An example of the packet-type products is disclosed in PCT Publication No. 82/02700. An example of the plastic-box type products is disclosed in U.S. Pat. No. 4,145,001. The instant invention is an improvement of products of the latter type.

Each of the three sorts of devices described above have certain disadvantages. For example, the bottle/wick products are bulky, expensive, and difficult to place in certain locations. The packet-type products do not provide a burst of fragrance (or other air-treating vapor) upon breaking of the inner capsule or bag, because the volatile composition must, after such breaking, migrate through the permeable film before any vapors are dispensed. Such a burst of fragrance is desirable in that it can overcome a malodor which may have prompted use of the product.

Both the packet-type products and the plastic-box type products may be susceptible to tampering by young children. Unless the contained volatile liquid is held within a mat or other absorbent material, there is some possibility of ingestion by young children. And, the use of an absorbent material to reduce ingestion concern eliminates the possibility of using the liquid as a visual use-up signal. An additional problem is the possibility of damaging finished surfaces if the permeable surface, through which the volatile composition passes, comes in contact with such surfaces.

There is a need for an improved continuous air-treatment device overcoming the aforementioned problems.

BRIEF SUMMARY OF THE INVENTION

This invention is an improved air-treating article of the type having an enclosure with a permeable film portion through which a volatile composition will permeate to be dispensed to the atmosphere as a vapor. In its preferred forms, the enclosure is a plastic tray with the film sealed to it around its edges. This might be considered a plastic-box type product.

The article includes a cover member (or "grill") which shields the permeable film from manual contact and from contact with other surfaces, such as finished surfaces. The cover member has openings to facilitate air movement against the permeable film. An impermeable strip is peelably adhered to the permeable film and is located under the cover member. This strip, as in certain products of the prior art, prevents dispensing of vapors until it is peeled away from the permeable film. A leader is attached at its proximal end to one end of the impermeable strip. From such attachment, the leader overlies the impermeable strip under the cover member and extends along the impermeable strip to terminate in a gripping end which is outside the cover member in position to be gripped and pulled for purposes of removing the impermeable strip.

In preferred embodiments, the volatile composition is a free liquid, that is, a liquid contained in the enclosure without an absorbent member. The permeable film and liquid have optical qualities which allow the liquid to be observed through the film. That is, the film is transparent or translucent to the extent that the liquid may be seen, perhaps by virtue of the coloring of the liquid. This provides a simple use-up indicator. Alternatively or in addition, the tray may be formed of a clear plastic for the same purpose.

The permeable film is preferably substantially in a single plane. In a highly preferred embodiment, the enclosure is formed of a plastic tray, preferably a thermoformed tray. In such embodiment, the tray, the permeable film (with its impermeable strip, prior to removal), and the cover member all have aligned edges which are secured together.

This invention allows the impermeable strip to be peeled away to expose the permeable film by pulling the leader while the cover member remains in place protecting the permeable film and making it inaccessible to small children. Further, the cover member can be designed to give a pleasing decorative appearance.

When the impermeable strip is removed, there is a burst of fragrance (or other air-treating vapor) because the permeable film, having been in contact with the volatile composition, is already saturated. The article of this invention is not easily susceptible to tampering by little children. Furthermore, the invention may readily be embodied in an inexpensive and non-bulky article which easily lends itself to placement in a variety of out-of-the-way locations. The invention makes an excellent "small spaces" air freshening device.

OBJECTS OF THE INVENTION

It is an object of this invention to provide a continuous vapor-dispensing device overcoming problems of the prior art.

Another object of this invention is to provide a vapor-dispensing device which resists tampering by young children.

Another object of this invention is to provide a vapor-dispensing device of the type having a permeable film, but which is child-safe and provides a burst of fragrance upon removal of an impermeable layer adhered to the permeable film.

Another object of this invention is to provide a vapor-dispensing device of the type having a permeable film to meter the dispensing of vapors and which does not have the risk of damaging finished surfaces.

Another object of this invention is to provide a vapor-dispensing device of the continuous type which is long-lasting.

Yet another object of this invention is to provide a vapor-dispensing device having the aforementioned advantages but which may readily be placed in relatively inaccessible locations.

These and other objects of this invention will be apparent from this specification and from the drawings, which include:

DETAILED DESCRIPTION OF PREFERRED EMBODIMENTS

Figure 2:
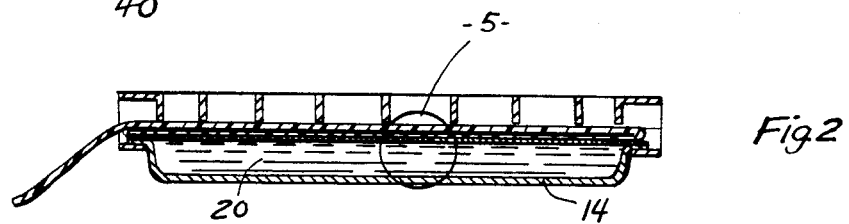
FIG. 2 is a side sectional view taken along section 2—2 as indicated in FIG. 1.
Figure 3:
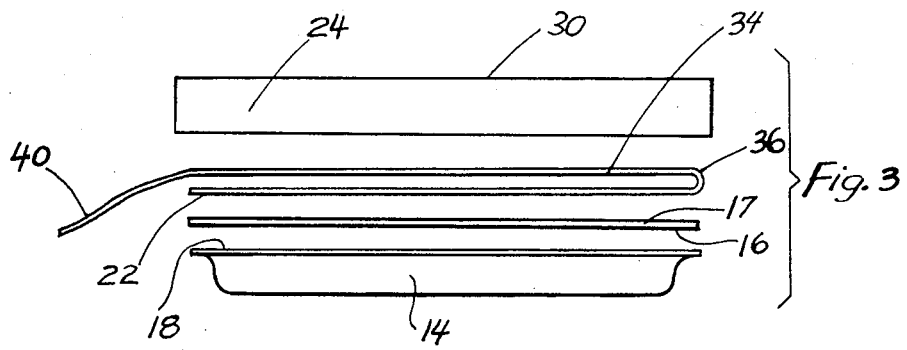
FIG. 3 is an exploded side view.
Figure 4:
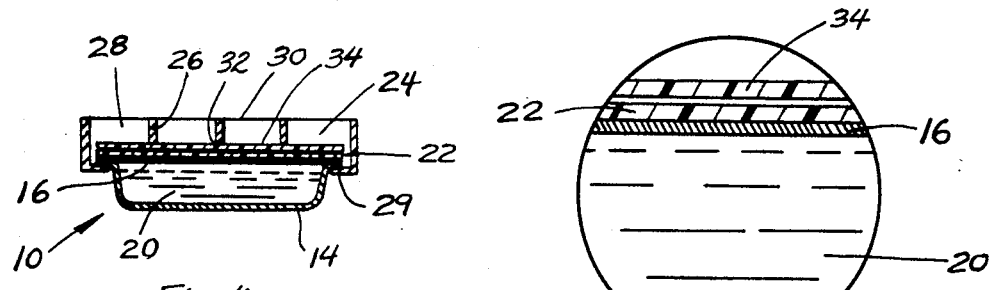
FIG. 4 is a rear sectional view taken along section 4—4 as indicated in FIG. 1.
Figure 5:
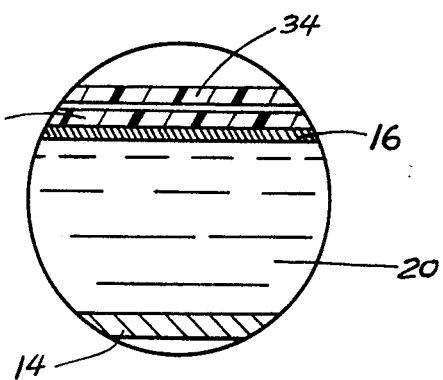
FIG. 5 is an enlarged fragmentary side sectional view as indicated in FIG. 2.

The figures illustrate a preferred air-treating article 10. Air-treating article 10 includes an enclosure 12 which is formed by tray 14 and film 16. Film 16 is sealed over tray 14 along edge 18 of tray 14. Contained within enclosure 12 is a volatile liquid 20, as illustrated in FIGS. 2, 4 and 5. Adhered to the outer surface 17 of film 16 is a strip 22 which prevents dispensing of the vapors of liquid 20 through film 16 until after its removal.

Film 16 is permeable to volatile liquid 20, such that after removal of strip 22 liquid 20 migrates through film 16 and is dispensed to the atmosphere as an air-treating vapor. Strip 22, prior to its removal, is adhered to film 16 along its entire surface by an adhesive (not shown). Strip 22 is impermeable to the volatile liquid, to prevent vapor dispensing as noted above. Strip 22 and film 16 form a laminate from which strip 22 may readily be peeled.

A cover member 24 is attached to enclosure 12 along the edges 18 of tray 14. Cover member 24 has cross members 26 forming a grill which serves to protect permeable film 16. Openings 28 are defined in cover member 24 between cross members 26. Openings 28 facilitate air movement against film 16.

As shown in FIGS. 2 and 4, cover member 24 includes opposing ledges 29 designed to receive tray 14 and to engage edges 18 of tray 14. Cross members 26 extend downwardly from the top 30 of cover member 24, but terminate in lower ends 32 at a position spaced above the level of film 16 to allow room for impermeable strip 22 and for leader 34, hereafter described.

Figure 1:
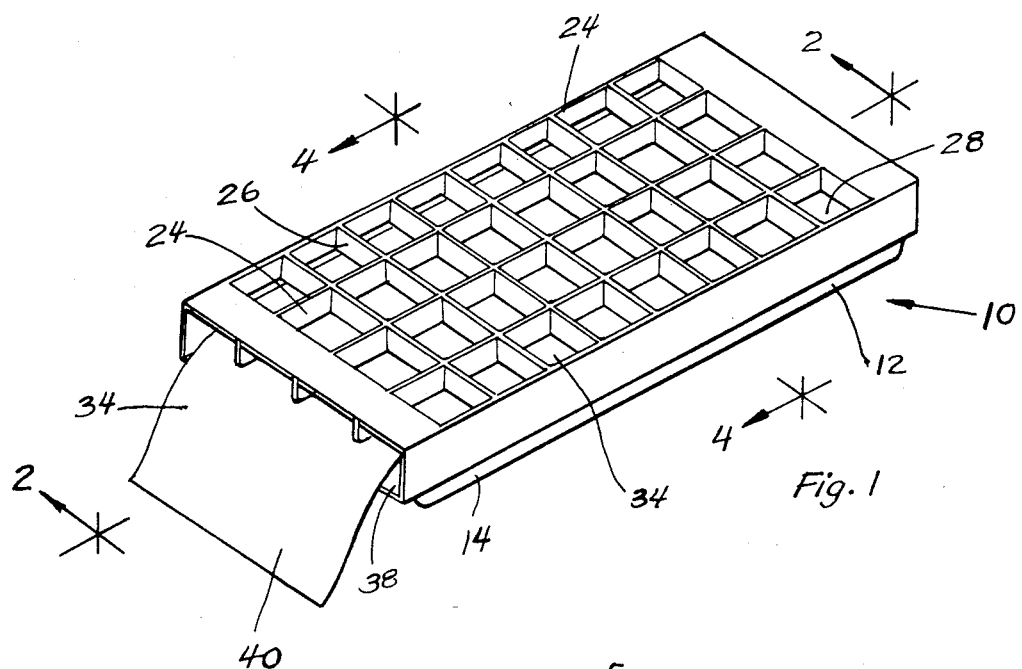
FIG. 1 is a perspective view of a preferred air-treating article in accordance with this invention.

Leader 34 is attached at its proximal end 36 to a first end 38 of impermeable strip 22. Leader 34 is doubled back over impermeable strip 22 such that it overlies strip 22 along the length thereof under cover member 24. Leader 34 exits at lateral opening 38 shown in FIGS. 1 and 2 and terminates in a gripping end 40 outside cover member 24. Leader 34 is preferably made integrally with peelable impermeable strip 22.

Volatile liquid 20 is free within enclosure 12, since no absorbent material is enclosed with it. Liquid 20 is preferably colored so that it may be more easily seen through film 16 after the removal of impermeable strip 22. Film 16 is preferably translucent or transparent to facilitate observation of the amount of liquid 20 remaining within enclosure 12. Such optical qualities of film 16 and liquid 20 provide a reliable use-up indicator.

Edge 18 of tray 14 are in a single plane such that permeable film 16 is substantially within a single plane. Tray 14, permeable film 16, and cover member 24 all have aligned edges which are secured together. This facilitates fabrication of this air-treating article. The laminate formed of permeable film 16 and impermeable strip 22 is heat sealed to tray edge 18 and, after tray 14 is slid onto ledges 29 of cover member 24, edges 18 of tray 14 are adhesively secured to ledges 29.

To activate the article of this invention for dispensing of air-treating vapors, article 10 is held in one hand and gripping end 40 of leader 34 is pulled by the other. This caused the peeling of impermeable strip 22 from film 16, beginning at the end remote from gripping end 40. Leader 34 and impermeable strip 22 are discarded and dispensing of air-treating vapors begins.

This invention is an air freshener product when fragrances are used. However, other volatile air-treating compositions may be used. One good example is insecticides.

The choice of packaging materials is dependent on the volatile liquid to be used. That is, the permeable film must, of course, be chosen to allow appropriate dispensing of such liquid, and the impermeable strip must be chosen to resist passage of such liquid. Specific liquids and materials are not the subject of this invention. However, one example would utilize a terpene based fragrance, a low-density polyethylene as the permeable film, and a coated aluminum foil as the impermeable strip. A wide variety of acceptable combinations would be known to those skilled in the art. Particular attention is drawn to the disclosure of the aforementioned Patent No. 4,145,001.

A wide variety of materials may be used for cover member 24, since there is little concern about chemical interaction between the liquid and this member. However, tray 14 must be of material impermeable to liquid 20. Tray 24 is preferably thermoformed and film 16 and strip 22 are preferably heat sealed thereover along edge 18.

While the principles of this invention have been described in connection with specific embodiments, it should be understood clearly that these descriptions are made only by way of example and are not intended to limit the scope of the invention.

What is claimed is:

1. In an air-treating article of the type having an enclosure with a permeable film portion which is nonporous and becomes saturated with a volatile composition, through which a volatile composition will permeate to be dispensed to the atmosphere as a vapor, the improvement comprising:

(a) a cover member covering the permeable film from manual contact and having openings to facilitate air movement against the film;

(b) an impermeable strip under the cover member and peelably adhered to the permeable film to prevent dispensing prior to peeling therefrom; and (c) a leader attached at its proximal and to one end of the impermeable strip, overlying the strip over the length thereof under the cover member, and terminating in a gripping end outside the cover member, whereby the impermeable strip may be peeled away to expose the permeable film by pulling the leader while the cover member remains in place to protect the permeable film.

2. The article of claim 1 wherein the volatile composition within the enclosure is a free liquid.

3. The article of claim 2 wherein the film and liquid have optical qualities such that the presence of the liquid can be seen through the permeable film, thereby providing a use-up indicator.

4. The article of claim 1 wherein the permeable film portion is substantially in a single plane.

5. The article of claim 4 wherein the enclosure comprises a plastic tray having the permeable film portion sealed thereover and the cover member is a plastic grill, the film, cover member and tray having aligned edges secured together.

6. The article of claim 5 wherein the volatile composition within the enclosure is a free liquid.

7. The article of claim 6 wherein the film and liquid have optical qualities such that the presence of the liquid can be seen through the permeable film, thereby providing a use-up indicator.

8. The article of claim 7 wherein the plastic tray is of clear plastic.

9. The article of claim 6 wherein the plastic tray is of clear plastic.

10. The article of claim 1 wherein the enclosure comprises a plastic tray having the permeable film portion sealed thereover and the cover member is a plastic grill, the film, cover member and tray having aligned edges secured together.

* * * * *

UNITED STATES PATENT AND TRADEMARK OFFICE
CERTIFICATE OF CORRECTION

PATENT NO. : 4,583,686

DATED : April 22, 1986

INVENTOR(S) : Edward J. Martens & Gerald H. Schuebel

It is certified that error appears in the above-identified patent and that said Letters Patent is hereby corrected as shown below:

In Claim 1, Column 4, Line 55, delete "and" and substitute therefore --end--.

Signed and Sealed this

Twentieth Day of October, 1987

*Attest:*

DONALD J. QUIGG

*Attesting Officer*  *Commissioner of Patents and Trademarks*